United States Patent
Fieres et al.

(10) Patent No.: US 9,033,859 B2
(45) Date of Patent: May 19, 2015

(54) METHOD AND DEVICE FOR DETERMINING A RADIOTHERAPY TREATMENT PLAN

(75) Inventors: Johannes Fieres, Heidelberg (DE); Oliver Thilmann, Heidelberg (DE)

(73) Assignee: Siemens Aktiengesellschaft, München (DE)

(*) Notice: Subject to any disclaimer, the term of this patent is extended or adjusted under 35 U.S.C. 154(b) by 262 days.

(21) Appl. No.: 13/419,031

(22) Filed: Mar. 13, 2012

(65) Prior Publication Data

US 2013/0072743 A1 Mar. 21, 2013

(30) Foreign Application Priority Data

Mar. 17, 2011 (DE) .......................... 10 2011 005 739

(51) Int. Cl.
*A61N 5/10* (2006.01)

(52) U.S. Cl.
CPC .............. *A61N 5/1031* (2013.01); *A61N 5/103* (2013.01)

(58) Field of Classification Search
CPC . A61N 5/1047; A61N 5/1031; A61N 5/1048; A61N 2005/1032; A61N 5/1049; A61N 5/1064
USPC .................... 600/407, 1, 3; 378/65
See application file for complete search history.

(56) References Cited

U.S. PATENT DOCUMENTS

| | | | |
|---|---|---|---|
| 7,268,358 B2 | 9/2007 | Ma et al. | |
| 7,298,819 B2* | 11/2007 | Dooley et al. | 378/65 |
| 7,982,200 B2 | 7/2011 | Keppel et al. | |
| 2003/0095625 A1* | 5/2003 | Steinberg | 378/65 |
| 2004/0165696 A1 | 8/2004 | Lee | |
| 2007/0201614 A1 | 8/2007 | Goldman et al. | |
| 2009/0060130 A1 | 3/2009 | Wilkens et al. | |
| 2010/0104068 A1 | 4/2010 | Kilby et al. | |

FOREIGN PATENT DOCUMENTS

EP 1 818 078 A1 8/2007

OTHER PUBLICATIONS

European Search Report dated Aug. 27, 2013 for corresponding European Patent Application No. 12152429.2 with English translation.
German Office Action dated Feb. 29, 2012 for corresponding German Patent Application No. DE 10 2011 005 739.0 with English translation.

(Continued)

*Primary Examiner* — Christine H Matthews
*Assistant Examiner* — Joshua D Lannu
(74) *Attorney, Agent, or Firm* — Lempia Summerfield Katz LLC

(57) ABSTRACT

A radiotherapy treatment plan for irradiation of an object to be irradiated is determined. The object to be irradiated includes a number of irradiation areas and the object to be irradiated is irradiated with a number of beams from different directions. The method includes determining a number of total dose conditions. One of the number of total dose conditions is assigned to a respective one of the number of irradiation areas. The method further includes determining a number of single beam dose conditions. One of the single dose conditions is assigned to a respective one of the number of beams and a respective one of the number of irradiation areas. The method also includes determining irradiation parameters for the number of beams as a function of the number of total dose conditions and the number of single beam dose conditions.

19 Claims, 9 Drawing Sheets

(56) References Cited

OTHER PUBLICATIONS

F. Albertini et al., "Degeneracy and Robustness of IMPT Plans in the Treatment of Skull-Base Chordomas," Medical Physics, vol. 34, No. 6, p. 2431, 2007.

M. Soukup et al., "Study of Robustness of IMPT and IMRT for Prostate Cancer Against Organ Movement," Int. J. Radiation Oncology Biol, Phys., vol. 75, No. 3, pp. 941-949, 2009.

M. Ellerbrock, "IMPT with Carbon Ions," PTCOG 48, Heidelberg, 28.09.-03.10.2009, Heidelberg Ion-Beam Therapy Center, pp. 1-30, 2009.

P. Lougovski et al., "Toward Truly Optimal IMRT Dose Distribution: Inverse Planning with Voxel-Specific Penalty," In: Technol. Cancer Res. Treat. 9, pp. 629-636, 2010.

T. Kim et al., "Inverse planning for IMRT with nonuniform beam profiles using total-variation regularization (TVR)," In: Med. Phys. 38, pp. 57-66, 2011.

* cited by examiner

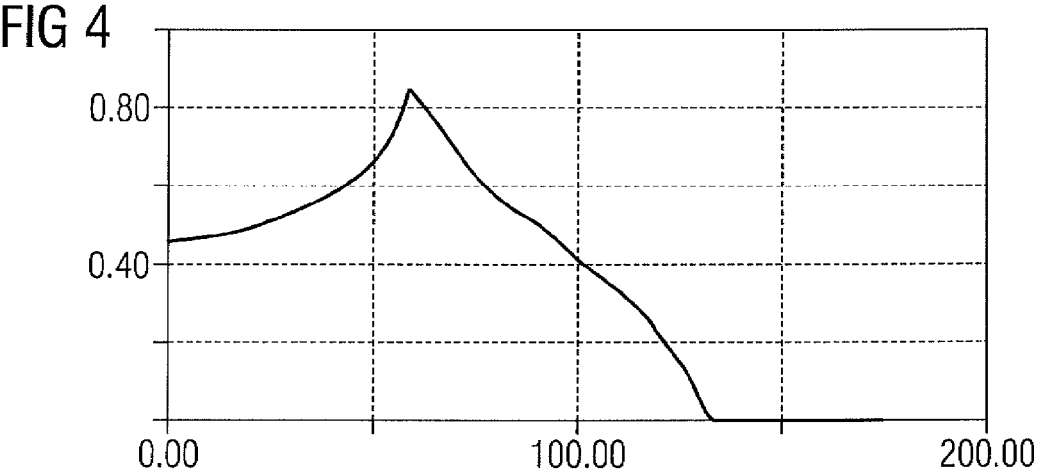
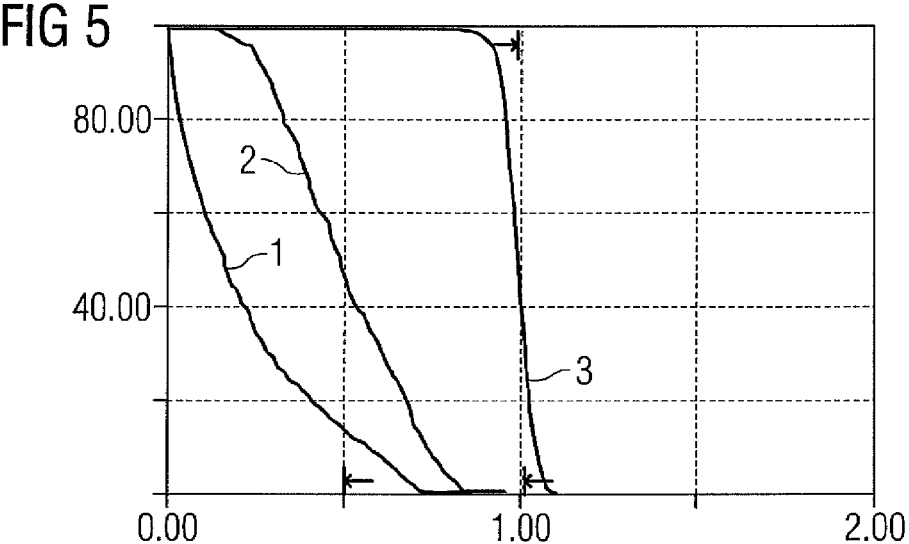
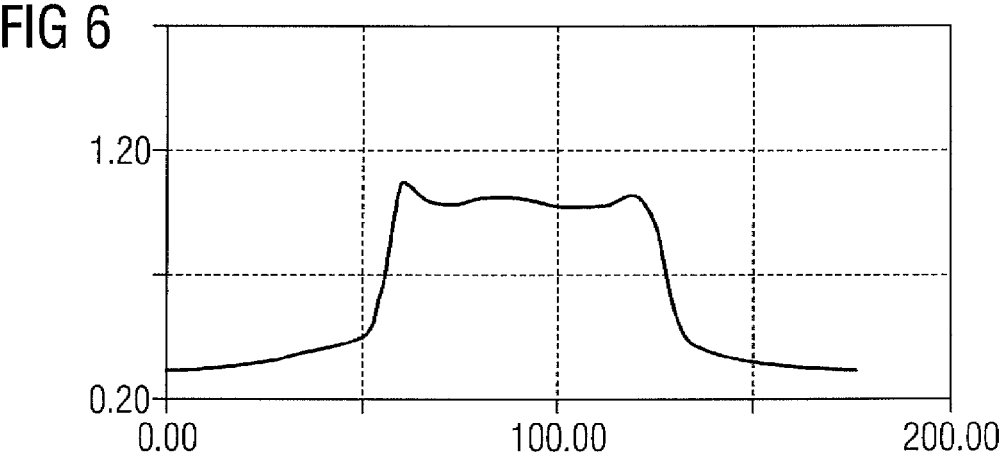

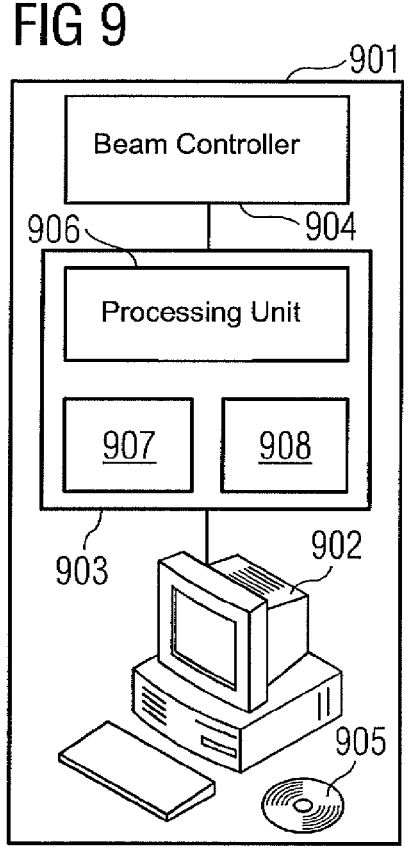
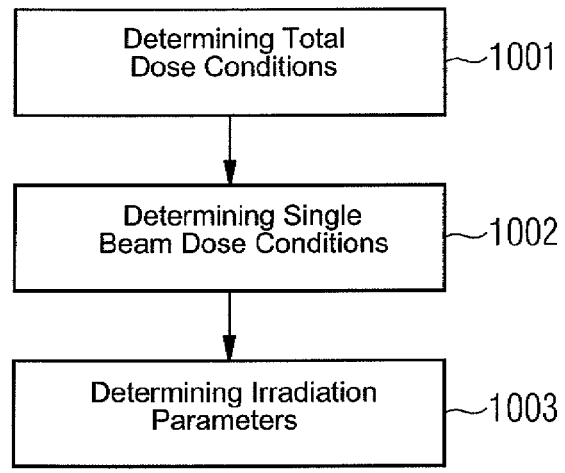
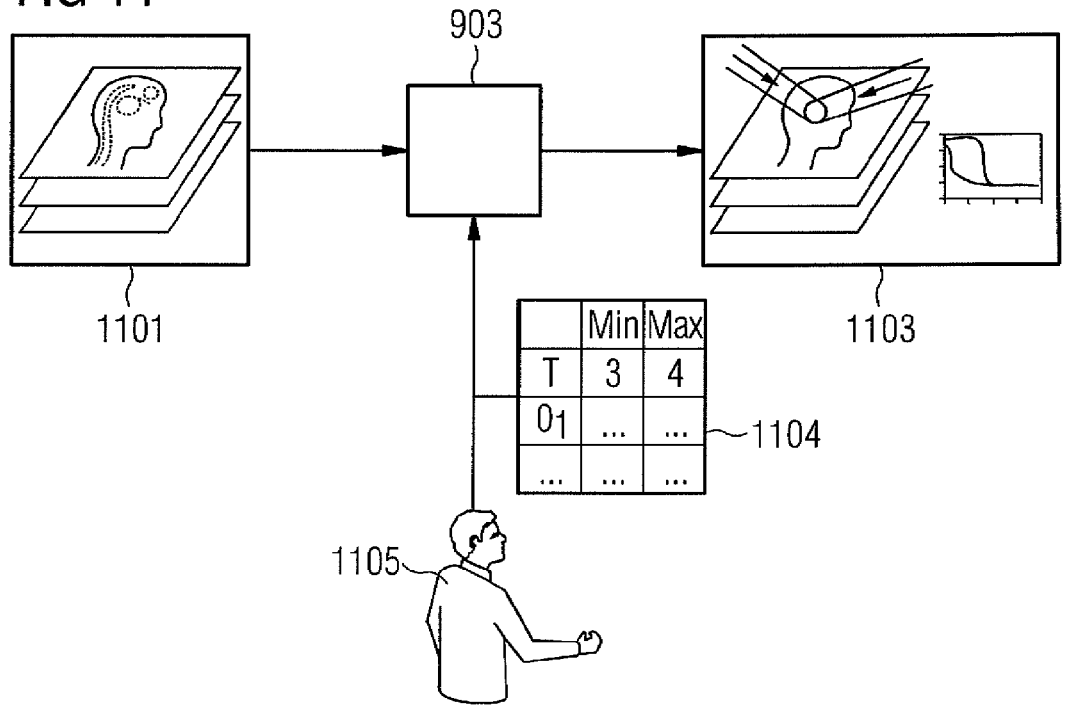

METHOD AND DEVICE FOR DETERMINING A RADIOTHERAPY TREATMENT PLAN

This application claims the benefit of DE 10 2011 005 739.0, filed Mar. 17, 2011.

BACKGROUND

The present embodiments relate to a method for determining a radiotherapy treatment plan for radiotherapy treatment of an object to be irradiated and to a corresponding device. The present embodiments further relate to a method for determining a radiotherapy treatment plan for radiation treatment of a patient with multiple beams as part of particle therapy (i.e., multi-beam particle therapy).

In multi-beam particle therapy, which is also known as multiple field therapy, radiation delivered from a number of beams with different angles of incidence is combined together into a conformant dose for distribution over a target volume. The particle fluence profiles of the beams will normally be determined by an automatic optimization method that operates on the basis of medical targets that are defined by a human user. These targets are usually expressed as conditions in relation to the resulting dose distribution. There are two principle approaches to specifying the dose conditions: either the user specifies the desired part doses of each beam separately, such that, for example, they are homogeneous over the target (single beam optimization, SBO), or the user specifies the desired sum dose of all beams (intensity-modulated particle therapy, IMPT) over the target. In IMPT, no conditions are imposed on the single beam doses and the single beam doses may thus be very inhomogeneous. Both methods, SBO and IMPT, which are shown below with reference to FIGS. 1-8, have their advantages and disadvantages.

FIG. 1 shows what is referred to as a dose-volume histogram, in which a radiation dose, measured in gray (Gy), is plotted on the x-axis and a tissue volume proportion, measured in terms of a percentage, is plotted on the y-axis. Graphs 1-3 each specify, for an area of tissue, a percentage of the respective tissue (y-axis) that receives a radiation dose based on the x-axis value or a value greater than the x-axis value. Such a dose-volume histogram (DVH) may, for example, be determined by a simulation for predetermined irradiation parameters before radiation therapy. In FIG. 1, graphs 1 and 2 show examples of a dose-volume histogram for sensitive areas of tissue or organs (i.e., for areas of tissue or organs which lie in the path of the radiation during radiation therapy but are to be irradiated as little as possible since the tissue or organs do not represent the target region of the radiation therapy). The objective is thus for these graphs to lie as far to the left as possible in the dose-volume histogram (i.e., to receive as little total radiation as possible and to receive the lowest possible maximum radiation). Graph 3, by contrast, shows the dose-volume histogram for a target region, such as, for example, a tumor region, which is also referred to as the Planning Target Volume (PTV). In order to obtain a homogenous and high irradiation of the target region, graph 3 in the dose-volume histogram of the target region should, if possible, fall away in steps at the desired target dose from 100% to 0%. With an ideal step, this would mean that 100% of the target region receives the desired radiation dose. In the dose-volume histogram of FIG. 1, the graph 3 deviates slightly from an ideal step function as a part of the target volume is irradiated with a radiation dose that is lower than the desired radiation dose of 1 Gy and another comparatively lower proportion of the target volume is irradiated with a radiation dose that is higher than the desired radiation dose.

FIG. 1 shows the dose-volume histogram which is created based on the IMPT method. The user pre-specifies 1 Gy as the desired radiation dose for the target region. In the example shown, the total dose for the target region is composed of two beams, which, for example, act on the target region from opposing directions. FIG. 2 shows the total dose over the irradiated region, with a size of the object or region to be irradiated in the patient plotted on the x-axis and the radiation dose, in gray (Gy), achieved in that portion of the object or region plotted on the y-axis. In the desired planning target volume (PTV) of, for example, 60 mm-120 mm, a comparatively homogeneous total dose of a good 1 Gy is achieved. FIGS. 3 and 4 show how the total dose of FIG. 2 is composed of the two beams. FIG. 3 shows the radiation dose as a result of a first beam, and FIG. 4 shows the radiation dose as a result of a second beam. A strong inhomogeneity of the individual beams in the planning target volume (PTV) is evident here. The first beam produces a very high radiation dose in the region between 100 and 120 mm, and the second beam produces a very high radiation dose in the region from 60 to 80 mm. This type of high beam inhomogeneity (i.e. widely differing doses of radiation resulting from individual beams), is, however, undesirable since the danger arises that overall, an inhomogeneous irradiation of the planning target volume results if the object to be irradiated is repositioned between the irradiation with the first beam and the irradiation with the second beam but the repositioning is not performed with sufficient accuracy. Repositioning during the treatment is only one possible error source. In particle radiation therapy, a globally incorrect positioning may also cause a displacement of the dose distributions relative to one another. Another error source is the product of patient geometry changes that occur when, for example, a patient loses weight between planning and treatment. In addition, there is the danger that sensitive tissue, which is to be irradiated as little as possible, receives an undesirably high radiation dose, especially after an insufficiently exact repositioning of the object to be irradiated. Although in principle the conventional IMPT produces a good and homogeneous irradiation of the target volume, as is evident from FIG. 1 and FIG. 2, and protects the sensitive healthy tissue during this process, the conventional IMPT is very susceptible to positioning errors and patient movements during the irradiation.

FIG. 5 shows a dose-volume histogram which is created with the aid of the SBO method. In FIG. 5, graphs 1 and 2 show radiation doses for sensitive tissue in the beam path, and graph 3 shows the radiation dose for the planning target volume (PTV). As is evident from FIG. 5, especially when compared with FIG. 1, the total coverage of the target volume with an even radiation dose is worse than with the IMPT method of FIG. 1. FIG. 6 shows the entire dose profile which is created by two opposing beams with the beam profiles of FIGS. 7 and 8. By comparing FIGS. 7 and 8 with FIGS. 3 and 4, it is shown that in the SBO method a higher single beam homogeneity may be achieved, so that the SBO method is more robust relative to planning and beam supply uncertainties or positional inaccuracies that occur while an object is repositioned between application of the first beam and of the second beam. In addition, homogeneous single doses are more robust relative to (initial) positioning errors.

Methods for optimizing either the IMPT method or the SPO method are thus known in the prior art. For example, Martin Soukup et al., in "Study of Robustness of IMPT and IMRT for Prostate Cancer against Organ Movement" (Int J Radiat Oncol Biol Phys. 75(3):941-9 (2009)), propose a method for initial beam weighting for an IMPT method in order to obtain better start conditions for the optimization.

Furthermore, F. Albertini et al., in "Degeneracy and Robustness of IMPT Plans in the Treatment of Skull-Base Chordomas" (Med. Phys. Volume 34, Issue 6, pp. 2431-2431 (2007)), propose that the IMPT method only be used as an entry point and, thus, that only a part of the total dose be delivered via the IMPT method and the majority of the dose be delivered via beams which have been optimized with the SBO method.

SUMMARY AND DESCRIPTION

The present embodiments may obviate one or more of the drawbacks or limitations in the related art. For example, improved methods for determining a radiotherapy treatment plan for an irradiation of an object to be irradiated with a number of beams may be provided.

In one embodiment, a method for determining a radiotherapy treatment plan for irradiation of an object to be irradiated is provided. A number of irradiation areas are determined in the object to be irradiated. The number of irradiation areas may, for example, include target areas to which an especially high radiation dose is to be applied and sensitive areas which are to receive a radiation dose that is as small as possible. An area to be irradiated may also be an individual pixel of, for example, a computer tomography image that serves as a basis for a radiotherapy treatment plan. The object to be irradiated is irradiated with a number of beams from different directions. The number of beams may, for example, be individually applied, one after the other, on the object to be irradiated. To achieve irradiation from the different irradiation directions, a direction of the beam may be changed, the object to be irradiated may be repositioned, or both the irradiation direction of the beam and the position of the object to be irradiated may be changed. The method further includes determining a number of total dose conditions, wherein at least one of the number of total dose conditions is assigned to a respective one of the number of irradiation areas. The total dose condition assigned to the respective irradiation area defines a condition for the total radiation dose for the corresponding irradiation area. Thus, each of the number of areas is assigned a total dose condition, a number of total dose conditions, or no total dose condition. Furthermore, a number of single beam dose conditions are determined. A single beam dose condition is assigned to one of the number of beams and the number of irradiation areas. The single beam dose condition assigned to the respective beam defines the condition for the radiation dose as a function of the beam for the respective irradiation area. Depending on the number of total dose conditions and on the number of single beam dose conditions, irradiation parameters are defined for the number of beams.

By taking into account both total dose conditions and single beam dose conditions when determining the irradiation parameters for the number of beams, the desired irradiation doses may be precisely set and achieved both in the target volume and also in sensitive volumes or volumes to be subjected to low radiation, and, at the same time, a homogeneity of the single beams may be improved, which enables the radiotherapy treatment plan to be more robust relative to planning and beam supply uncertainties.

In one embodiment, the irradiation parameters for the number of beams are determined using an optimization method. In the optimization method, a target function is minimized as a function of the irradiation parameters and the conditions.

In one embodiment, a user input assigns each of the number of irradiation areas a total dose condition, and, thus, determines the number of total dose conditions.

In another embodiment, the single beam dose conditions may be determined by a detected user entry. The user entry assigns a respective single beam dose condition to the number of beams for each one of the irradiation areas.

Since the total dose conditions and the single beam dose conditions may be entered by a user, very precise and detailed radiotherapy treatment planning is possible.

In one embodiment, the number of single beam dose conditions are automatically determined as a function of a predetermined beam homogeneity factor. The beam homogeneity factor defines, for one of the number of irradiation areas or for all of the irradiation areas, a maximum difference between the radiation doses introduced into the irradiation area by the number of beams. Depending on the beam homogeneity factor, corresponding single beam dose conditions may be, for example, automatically determined for the individual beams. The beam homogeneity factor may either be a fixed pre-specified factor or may be adjusted via a user input.

Furthermore, a user input that includes abeam homogeneity weighting may be detected by a user input. The beam homogeneity weighting is used during the determination of the irradiation parameters. The beam homogeneity weighting, in this embodiment, specifies a measure for taking account of the single beam dose conditions during the determination of the irradiation parameters. The irradiation parameters for the number of beams may be optimized by minimizing a target function. The target function in this embodiment is dependent on the beam homogeneity factor or the single beam dose conditions derived therefrom, the beam homogeneity weighting, and the total dose conditions.

The fact that the single beam dose conditions may be determined automatically from the beam homogeneity factor enables a significant reduction in the number of parameters that need to be input by a user in the determination of the radiotherapy treatment plan. Accordingly, a radiotherapy treatment plan may be determined more quickly and may represent a less complex task for the user. Depending on the beam homogeneity weight, the user may, depending on the application, increase or reduce the beam homogeneity in a simple manner.

In one embodiment, a dose distribution for a beam is determined based on a predetermined minimum total dose level, a predetermined maximum total dose level, the homogeneity factor, and the number of beams. This enables corresponding single beam dose conditions, relative to the maximum value and the minimum value for the beam, to be determined from the beam homogeneity factor in a simple manner.

In one embodiment, a user input of a single beam weighting is also recorded. The irradiation parameters are determined for each of the number of beams as a function of the number of total dose conditions, the number of single beam dose conditions, and the single beam weighting. The single beam weighting specifies a relationship between the single beam dose conditions and the total dose conditions during the determination of the irradiation parameters. This makes it possible for a user, depending on the application, to take greater account of the single beam dose conditions or the total dose conditions. This may, for example, allow for improved protection of healthy tissue not to be irradiated or permit a more robust design of the radiotherapy treatment plan relative to planning and supply uncertainties.

In one embodiment, a number of beam-specific irradiation areas are determined in the object to be irradiated and the irradiation parameters are determined for the number of beams as a function of whether the beam-specific irradiation areas overlap. For irradiation areas in which the beam-specific irradiation areas overlap, the irradiation parameters are determined as a function of the total dose condition for these areas, while for radiation areas in which the dose-specific irradiation areas do not overlap, the irradiation parameters are determined as a function of the single beam dose conditions. This ensures that a healthy tissue area that is not to be irradiated is reliably spared and, simultaneously, target areas that are only to be irradiated by one beam are reliably irradiated.

In one embodiment, user-specific beam weightings of the individual single beam dose conditions may be added. The user-specific beam weightings increase or decrease the importance or weighting of the corresponding single beam dose condition during the optimization of the radiotherapy treatment plan.

A total beam dose condition may, for example, be specified as or in terms of a maximum dose, a minimum dose, a dose-volume histogram, an average dose, or a beam homogeneity. A single beam dose condition may, for example, be specified as or in terms of a maximum dose, a minimum dose or an average dose.

In another embodiment, a device for determining a radiotherapy treatment plan for irradiation of an object to be irradiated may be provided. A number of irradiation areas are determined in the object to be irradiated. The object under irradiation is irradiated with a number of beams from different directions. The device includes a first determination device for determining a number of total dose conditions. At least one of the number of total dose conditions is assigned to a respective one of the number of irradiation areas. The total dose condition assigned to the respective irradiation area defines a condition for the total radiation dose for the irradiation area. The device further includes a second determination device for determining a number of single beam dose conditions. One of the number of single beam dose conditions is assigned to a respective one of the number of beams and a respective one of the number of radiation areas. The single beam dose condition assigned to the respective beam defines a condition for the radiation dose based on the beam for the respective irradiation area. Finally, the device includes a processing unit that is configured to determine irradiation parameters for the number of beams as a function of the number of total dose conditions and the number of single beam dose conditions.

In one embodiment, the device is configured to perform the previously described method and all of its embodiments and thus also includes the advantages previously described in connection therewith.

In another embodiment, a particle therapy system that includes previously described device may be provided. Consequently, the particle therapy system provides the same advantages described in connection with the method described herein.

Furthermore, a computer program product, particularly a computer program or software that can be loaded into a memory of a programmable processing unit of a device for determining a radiotherapy treatment plan, may also be provided. One or more of the previously described embodiments of the method may be executed with this computer program product when the computer program product is running in the processing unit. The computer program product may use programming means, such as, for example, libraries and auxiliary functions, in order to implement one or more of the corresponding embodiments of the method described herein. In one embodiment, the software may involve source code (e.g., C++) that has to be compiled (i.e. translated) and linked or that only has to be interpreted, or the software may involve an executable software code that only has to be loaded into the corresponding processing unit for execution.

Finally, an electronically-readable data medium, such as, for example, a DVD, a magnetic tape, or a USB stick, on which electronically-readable control information, particularly software as described above, is stored may be provided. When this control information or software is read from the data medium and stored in the processing unit, one or more of embodiments of the method described herein may be executed.

BRIEF DESCRIPTION OF THE DRAWINGS

FIG. 4 shows a dose profile of a second beam of an irradiation determined with the IMPT method of FIG. 1;

FIG. 5-8 show a dose-volume histogram, a total dose profile, a dose profile of a first beam, and a dose profile of a second beam for a radiotherapy treatment plan created using an SBO method;

FIG. 9 shows one embodiment of a particle therapy system;

FIG. 10 shows a flow diagram of one embodiment of a method for determining a radiotherapy treatment plan;

FIG. 11 shows a schematic diagram that illustrates the execution of the method for determining a radiotherapy treatment plan shown in FIG. 10;

DETAILED DESCRIPTION OF THE DRAWINGS

Figure 1:
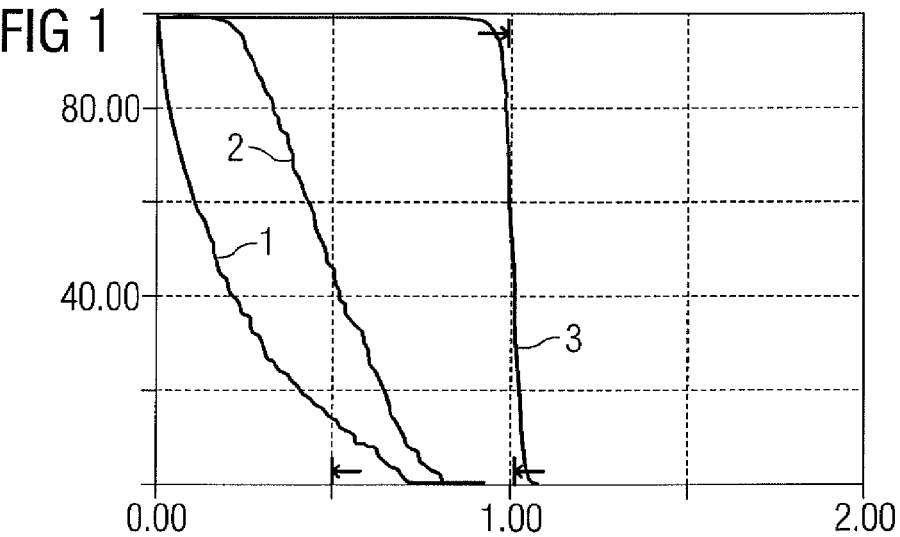
FIG. 1 shows a dose-volume histogram for a radiotherapy treatment plan created using an IMPT method.
Figure 2:
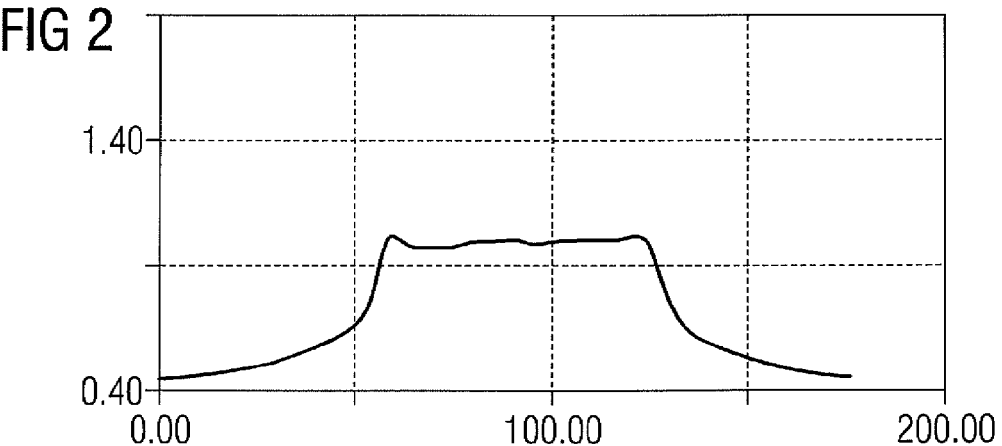
FIG. 2 shows the total dose profile for an irradiation determined with the IMPT method of FIG. 1.
Figure 3:
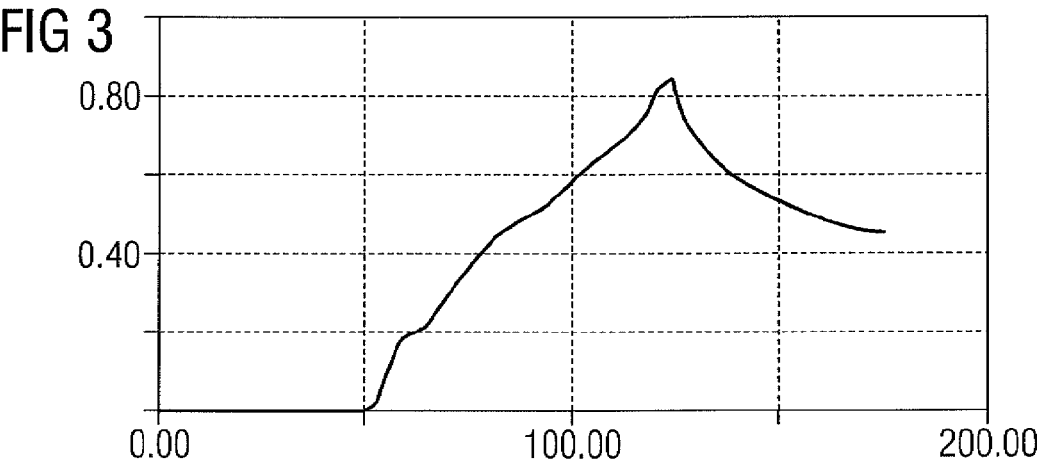
FIG. 3 shows a dose profile of a first beam of an irradiation determined with the IMPT method of FIG. 1.
Figure 7:
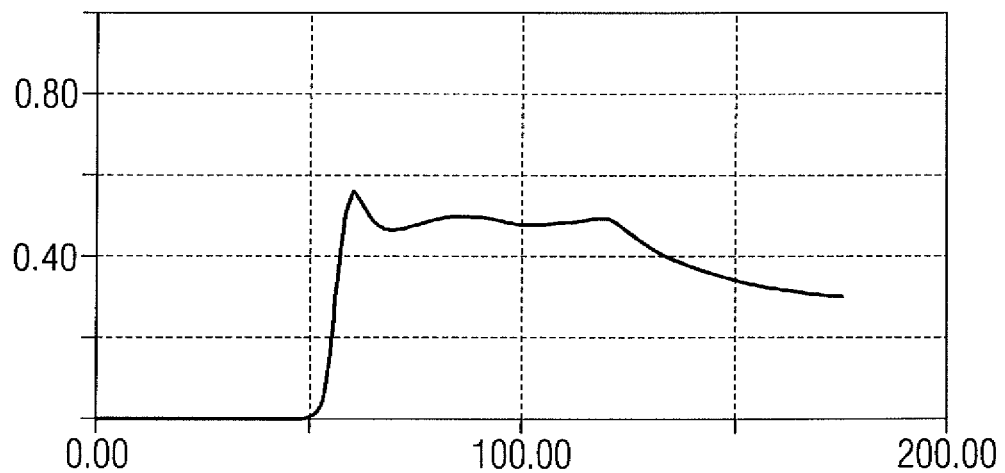
Figure 8:
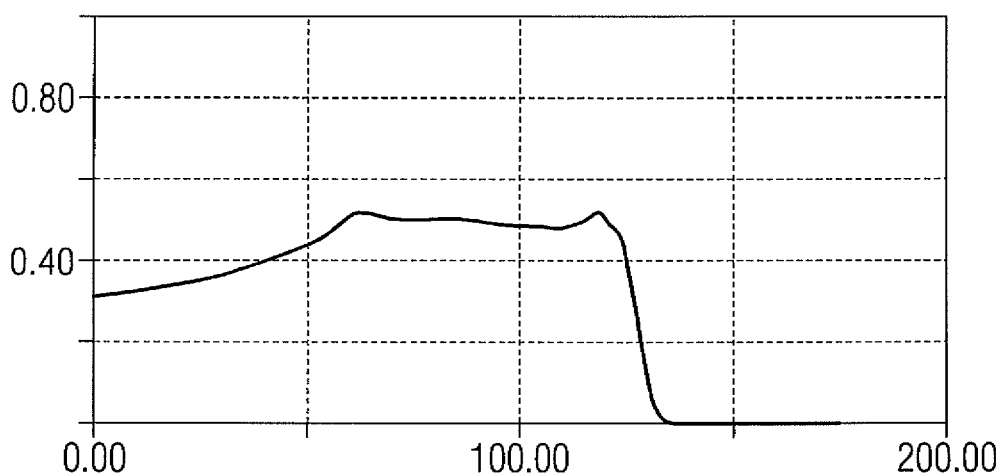

FIG. 9 shows a particle therapy system 901 that includes a user interface 902, a device for determining a radiotherapy treatment plan 903, and a beam controller 904. The user interface 902 may, for example, include a screen and keyboard. Furthermore the user interface 902 may include a read device for reading an electronically-readable data medium 905 on which programs for the user interface 902 and the device 903 are stored. The device 903 includes a processing unit 906, a first determination unit 907, and a second determination unit 908. The processing unit 906 and the determination units 907, 908 may alternatively be combined into one integrated unit.

Referring to FIGS. 10 and 11, the operation of the particle therapy system 901 will now be described in greater detail. On the basis of image slices 1101, which are, for example, magnetic resonance images or computed tomography images, fundamentals of a therapy plan are determined. In this embodiment, the image slices 1101 are segmented into regions which, for example, differentiate tumor regions and organ regions. Furthermore, the number of the beams and their respective direction for the irradiation of the tumor region is defined. Furthermore, conditions for the radiotherapy treatment plan are entered by a user 1105 via the user interface 902. These conditions may, for example, be recorded in the form of a table 1104. Total dose conditions are pre-specified for selected areas (act 1001) and selected beams are assigned single beam dose conditions for selected areas (act 1002). In the table 1104 shown in FIG. 11, a minimum value (Min) and a maximum value (Max) are assigned for each respective tumor area (T). In addition, each further area (e.g. an organ area with the designation $O_1$), determined during the segmentation of the image slices 1101, is assigned corresponding conditions. Thus, a number of tumor areas and a number of non-tumor areas may be provided with corresponding total dose conditions and single beam dose conditions. The non-tumor areas are also referred to herein as sensitive areas and should receive a radiation dose that is as small as possible. The total dose conditions are provided to the processing unit 906 by the first determination unit 907, and the single beam dose conditions are provided to the processing unit 906 by the second determination unit 908. In act 1003, irradiation parameters are determined by the device 903, using an optimization method, based on the total dose conditions, the single beam dose conditions, and the areas defined in the slice images 1101. Based on the irradiation parameters, a dose-volume histogram for the different areas may be simulated and output via the user interface 902 to a user 1105. In addition, a radiotherapy treatment plan 1103 may be created, based on the irradiation parameters, and may be used by a beam controller 904 during irradiation of the patient.

Dose conditions are used as an input for the optimization method, with each condition being related either to the total dose of an area or to one of the single beam doses. The overall target function for the optimization of the irradiation parameters p for the number of beams is thus as follows:

$$F(p) = F_{tot}(p) + \sum_i F_i(p)$$

The first summand ($F_{tot}(p)$) is an evaluation function that represents a fulfillment of the total dose conditions for the irradiation parameters p. The second summand $$\left( \sum_i F_i(p) \right)$$

is a sum of all beams i and $F_i(p)$ is an evaluation function that represents a fulfillment of the single beam dose conditions for the beam i in the radiation parameters p.

The function F(p) may, for example, be defined via differences for desired dose conditions as follows:

$$F(p) = diff(D_{tot,desired}, D_{tot,act}(p)) + \sum_i (diff(D_{i,desired}, D_{i,act}(p)))$$

For the first summand ($diff(D_{tot,desired}, D_{tot,act}(p))$), the user specifies conditions relative to the total dose. For example, the user sets one or more conditions for specific volumetric structures (e.g., organs or the target area). The conditions typically include a maximum allowed dose, a minimum allowed dose, a statically defined dose-volume histogram, or a desired average dose. The total dose may thus also include a distribution function of the dose for the structure. In the first summand, p is the beam parameter, $D_{tot,desired}$ is the total desired dose, $D_{tot,act(p)}$ is the calculated dose of the current optimization step, and the function diff( ) is a measure of the difference between the two doses. $D_{tot,desired}$ is implicitly defined by the dose conditions set. The second summand $$\left( \sum_i (diff(D_{i,desired}, D_{i,act}(p))) \right)$$

is a sum of all beams i. $D_{i,desired}$ is implicitly defined by the selected single beam dose conditions. $D_{i,act}$ is the calculated dose of a beam i for the current optimization step. As in the first summand, the function diff( ) is a measure of a difference between the two doses. The target function F(p) may be, for example, minimized iteratively. In addition, each of the previously mentioned conditions, i.e. each total dose condition and each single beam dose condition, may be provided with an individual weight that makes it possible to set a relative weighting of the single beam dose condition or total dose condition. The user may choose, for each condition, whether the weighting applies to the total dose or to one of the single beam doses.

Manually setting the conditions is, however, a comparatively complex task for the user. The embodiment depicted in FIG. 12 simplifies this task. A further device 1201, which may, for example, be integrated with the processing unit 906, creates the total dose conditions and the single beam dose conditions of table 1104. To this end, the user 1105 enters conditions relating to the total dose (e.g., a minimum condition and a maximum condition for the target volume) into the device 1201. In addition, the user enters two further parameters. The first parameter is a homogeneity factor HF, which is selected, for example, from a range of between 0 and 1. The second parameter is a beam homogeneity weighting HW. The homogeneity factor HF is translated by the device 1201 into additional conditions for the single beam doses. The overall target function F(p), which is now to be minimized, thus becomes:

$$F(p) = F_{tot}(p) + HW \cdot \sum_i F_i(p, HF)$$

The first summand ($F_{tot}(p)$) is an evaluation function that represents a fulfillment of the total dose conditions for the irradiation parameters p and $F_i(p,HF)$ is an evaluation function that is determined by the beam homogeneity factor HF and represents a fulfillment of the single beam dose conditions for the beam i in the irradiation parameters p.

The function F(p) may, for example, again be defined via differences from desired dose conditions as follows:

$$F(p) = diff(D_{tot,desired}, D_{tot,act}(p)) + HW \cdot \sum_i (diff(D_{i,desired}(HF), D_{i,act}(p)))$$

Single beam dose conditions $D_{i,desired}$ (HF), for example, for each beam i, a minimum condition $D_{min,i}$, and a maximum condition $D_{max,i}$ may be defined and automatically determined by the device 1201:

$$D_{max,i} = D_{max,tot} * (1 - HF/B)$$

$$D_{min,i} = D_{min,tot} * HF/B$$

wherein $D_{max,tot}$ and $D_{min,tot}$ are the maximum and minimum total dose levels, respectively, pre-specified by the user for the target volume, and $D_{max,i}$ and $D_{min,i}$ are the derived minimum and maximum beam dose levels, respectively, for the target volume. B is the number of beams involved at the target volume. For areas outside the target area, i.e. the sensitive areas, only the conditions of the total dose apply. In one embodiment, user-selectable beam weights may be used in the above equations. With a total of two beams (B=2) and when $D_{max,tot}=D_{min,tot}$ and HF=1, each beam is required to deliver 50% of the desired target dose. When HF=0.5 but all of the other parameters are the same, each beam is required to deliver not more than 75% and not less than 25% of the desired target dose. If HF is set to zero but all of the other parameters are the same, no additional conditions are produced for the single beam doses.

The beam homogeneity weighting makes it possible to weight the effect of the single beam dose conditions. When HW=0, the conditions do not affect the single beam doses.

Figure 12:
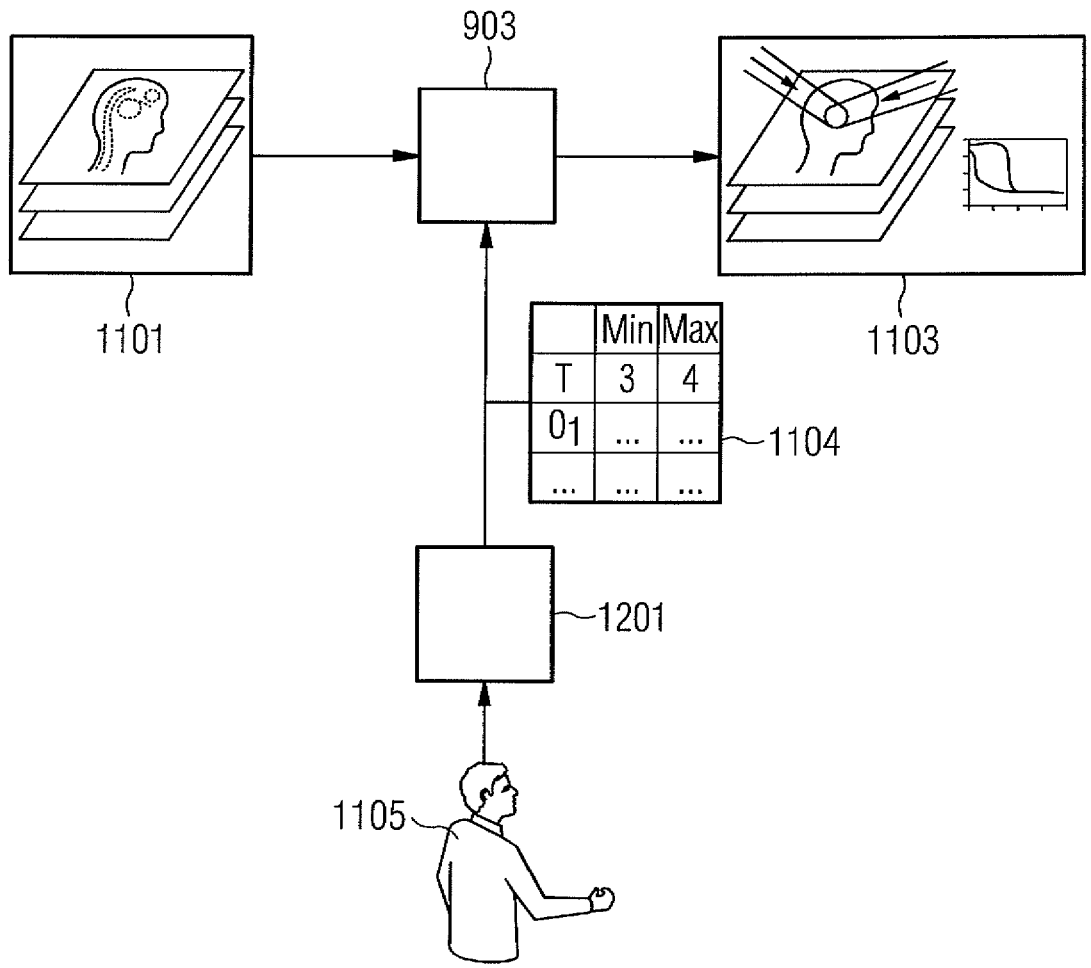
FIG. 12 shows a schematic diagram that illustrates the execution of another embodiment of a method for determining a radiotherapy treatment plan.

Unlike the method described in connection with FIG. 11, the user, in the method described in connection with FIG. 12, may set any different requirements for each beam and, thus, does not have to choose any fine-granular conditions. The configuration is thus simpler overall and the beam homogeneity weighting HW makes it possible for the user to globally control the influence of the single beam dose conditions.

In an alternative embodiment, the homogeneity factor HF may also be a fixed value predetermined by the system.

In a further embodiment, the user, as has been described above, may set the total dose conditions, the single beam dose conditions, and a relative single beam weighting W. W may, for example, be set within a range of 0 to 1. The target function F(p), which is minimized to determine the irradiation parameters for the number of beams, is expressed as follows in this embodiment:

$$F(p) = (1-W) \cdot F_{tot}(p) + W \cdot \sum_i F_i(p)$$

The first summand ($F_{tot}(p)$) is an evaluation function that represents a fulfillment of the total dose conditions in the irradiation parameters p, and $F_i(p)$ is an evaluation function that represents a fulfillment of the single beam dose conditions for the beam i in the irradiation parameters p.

The function F(p) may, for example, be defined via differences from desired dose conditions as follows:

$$F(p) = (1-W) \cdot \text{diff}(D_{tot,desired}, D_{tot,act}(p)) + W \cdot \sum_i (\text{diff}(D_{i,desired}, D_{i,act}(p))$$

Thus, greater account may be taken of either the single beam dose conditions (first summand) or the total dose conditions (second summand) via the single beam weighting W. The first summand corresponds to an optimization strategy that uses an IMPT method and the second summand corresponds to an optimization strategy that uses an SPO method.

Figure 13:
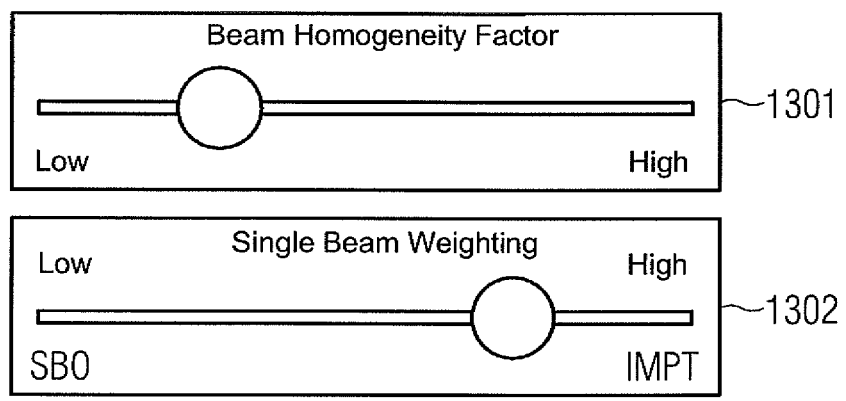
FIG. 13 shows one embodiment of two control elements of a graphical user interface.

FIG. 13 shows graphic control elements of the user interface 902 for adjusting the beam homogeneity factor HF using a slider 1301 and for adjusting the single beam weighting using a slider 1302.

In one embodiment, the user may define a separate target region for each beam. These target regions overlap to very large extent but still differ slightly from each other. As previously described, the user may define total dose conditions for the target region and normal organs or sensitive regions. Based on this information, those conditions are created by the device 903 as follows: In areas in which the target regions intersect, the total dose conditions are applied, and in the areas that are only relevant for a beam i, single beam conditions are applied for the beam i, with $D_i=D_{target}/B$. In one embodiment, the user may weight the single beam conditions. In regions with normal organs or sensitive regions, the total dose conditions are applied. As such, the advantages of an IMPT method are combined with the advantages of beam-dependent target areas.

Figure 14:
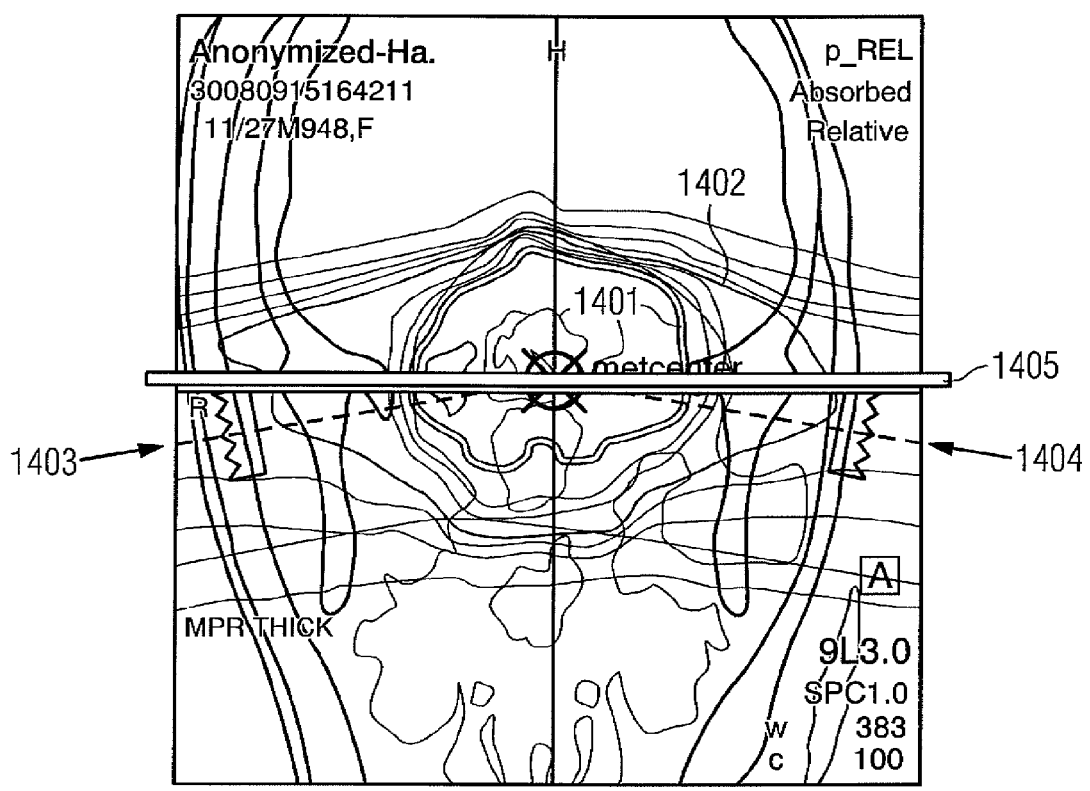
FIG. 14 shows a sectional image of the head of the patient with areas of different radiation intensity marked therein.

FIG. 14 shows an image slice of a head. The target area (e.g., a tumor) is located in the center of the image. The polylines drawn on the image delimit regions of the same radiation intensity. For example, the polylines 1401 and 1402 are identified by reference numbers. The head is irradiated by two particle beams in the direction of the arrows 1403 and 1404. Also shown in FIG. 14 is a cut line 1405 that will be used with reference to FIG. 15-22.

Figure 15:
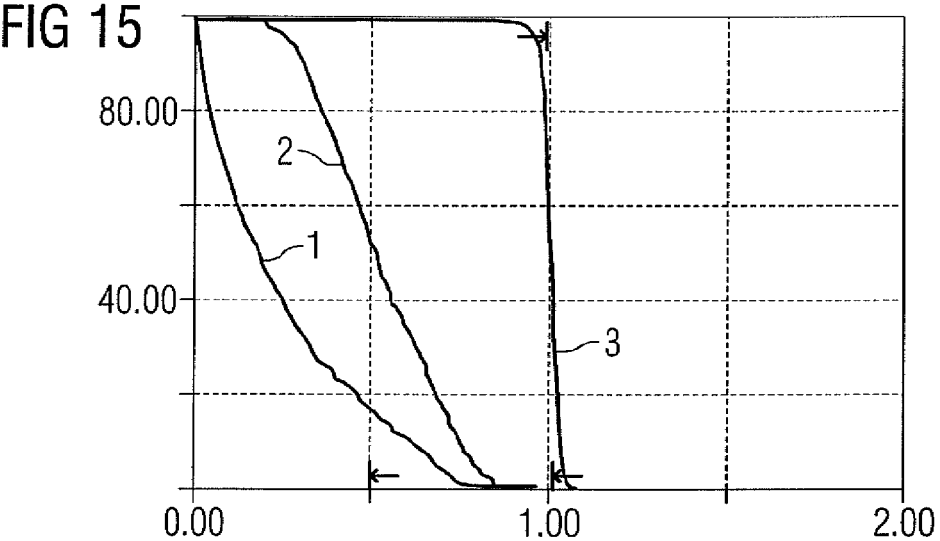
FIG. 15-18 show a dose-volume histogram, a total dose profile, a dose profile of a first beam, and a dose profile of a second beam determined using the method shown in FIG. 12.
Figure 16:
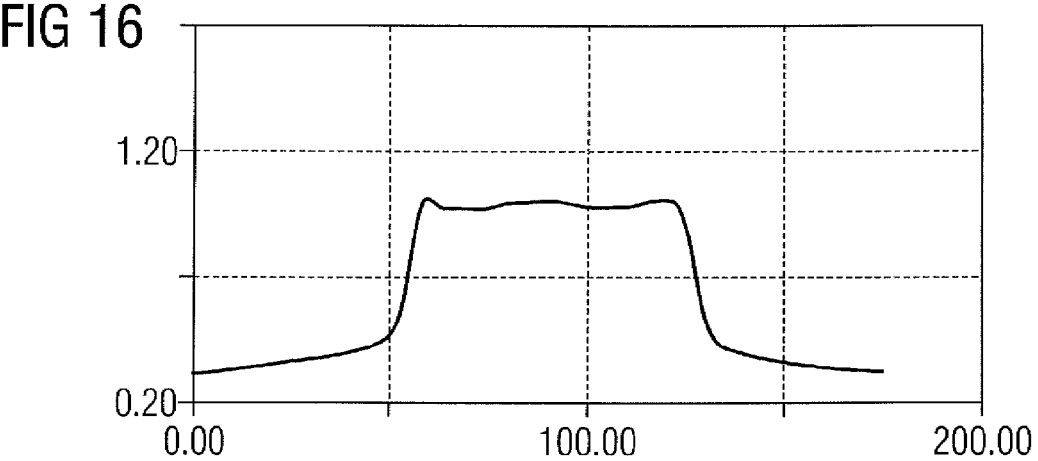
Figure 17:
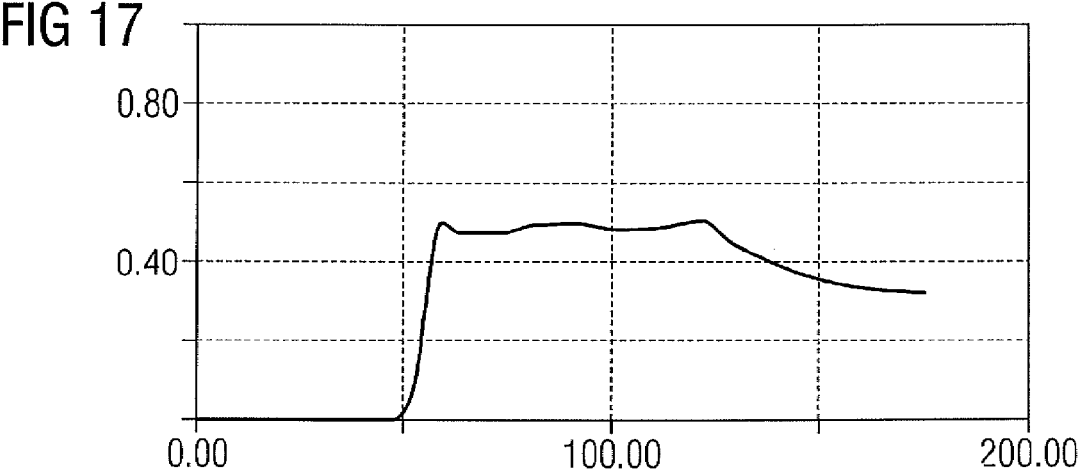
Figure 18:
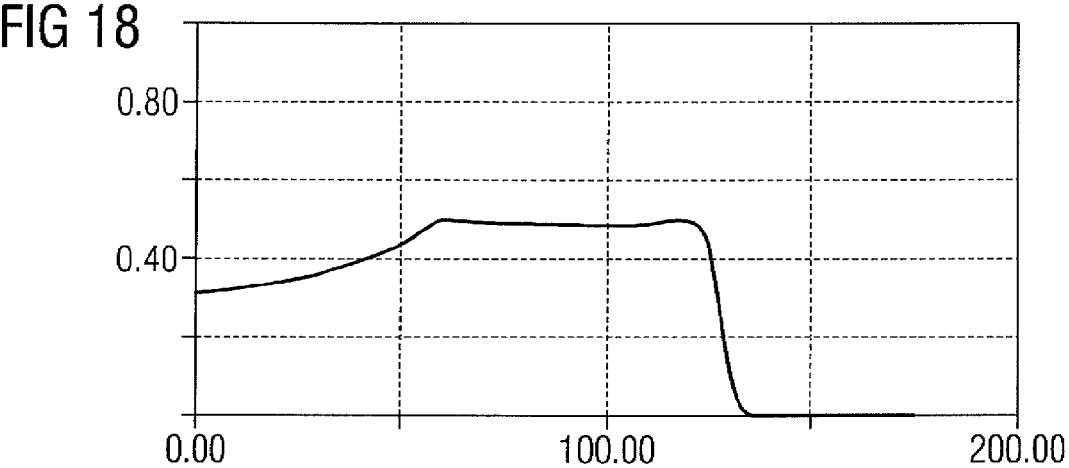

FIG. 15 shows a dose-volume histogram for a radiotherapy treatment plan determined using the embodiment described in connection with FIG. 12. The homogeneity factor is set to HF=1 and the beam homogeneity weighting is set to HW=1. The steep step of the graph 3 for the target region or the tumor may be seen in FIG. 15. The sensitive organs are significantly less stressed, as is shown in graphs 1 and 2. The homogeneity factor HF=1 aims for an even intensity distribution of the individual beams. FIG. 16 shows the total dose profile, and FIGS. 17 and 18 show the dose profiles of beams 1404 and 1403. The homogeneous dose distribution between the beams 1404 and 1403 may be seen in FIGS. 17 and 18. Each of the two beams contributes, as is required when HF=1, approximately 50% of the total radiation dose.

Figure 19:
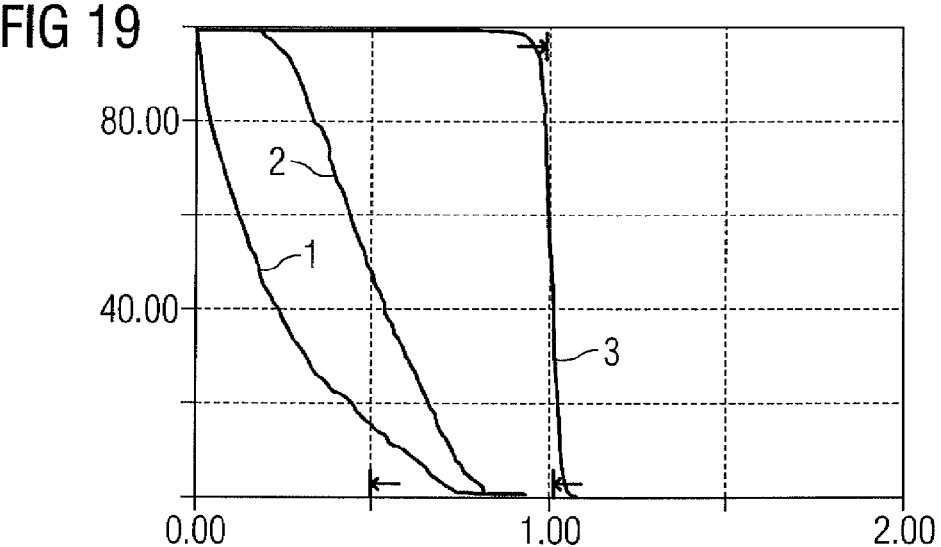
FIG. 19-22 show a dose-volume histogram, a total dose profile, a dose profile of a first beam, and a dose profile of a second beam determined using another embodiment of a method for determining a radiotherapy treatment plan.
Figure 20:
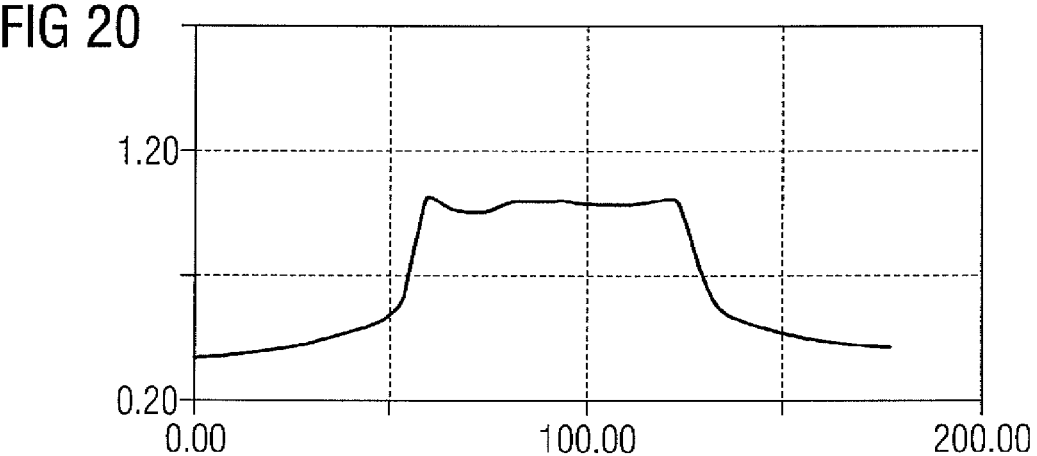
Figure 21:
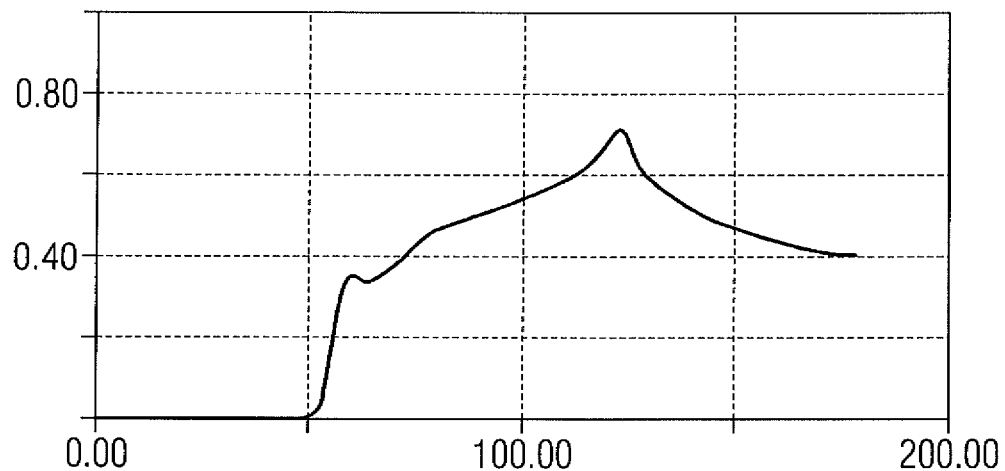
Figure 22:
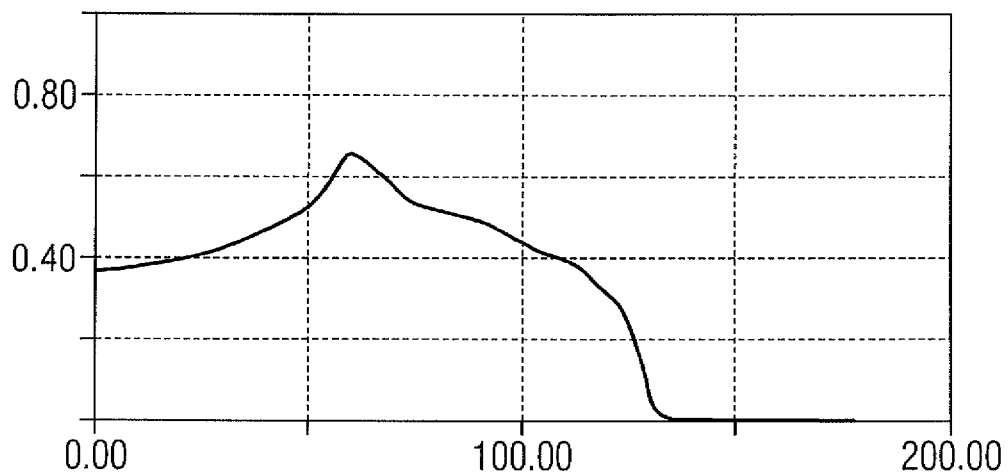

FIG. 19 shows a dose-volume histogram for a homogeneity factor of HF=0.6 and a beam homogeneity weighting of HW=1. By comparison with the dose-volume histogram of FIG. 15, in FIG. 19 the sensitive regions are less heavily stressed, as can be seen from the position of the graphs 1 and 2. The total dose profile shown in FIG. 20 is comparable to the total dose profile shown in FIG. 16. The dose profile of the beam 1404 is shown in FIG. 21 and the dose profile of the beam 1403 shown in FIG. 22. FIGS. 21 and 22 exhibit a greatly increased beam homogeneity as compared with the homogeneous dose distribution shown in FIGS. 17 and 18. The individual doses do not, however, exceed a corridor of 30%-70%. This is ensured by the homogeneity factor HF=0.6.

The user may thus control the single beam dose distributions and, at the same time, benefit from the advantages of an IMPT method. In addition, the user may define beam-dependent target regions. As is evident from FIGS. 15-22, a very good target coverage may be achieved and, at the same time, a desired homogeneity of the single beam doses may be achieved.

Although the present invention in the above description has essentially been described in combination with radiotherapy treatment planning of a particle therapy, the methods of the present invention are however equally suitable for determining a radiotherapy treatment plan for a general radiotherapy using, for example, gamma radiation, photon radiation, or x-radiation.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a radiotherapy treatment plan for an irradiation of an object to be irradiated, wherein a number of irradiation regions are determined in the object to be irradiated, and wherein the object to be irradiated is irradiated with a number of beams from different directions, the method comprising:
providing a processor configured for determination of dose conditions and determination of irradiation parameters for the number of beams as a function of a number of total dose conditions and a number of single beam dose conditions;
determining, by the processor, the number of total dose conditions, wherein at least one of the number of total dose conditions is assigned to a respective one of the number of irradiation regions, and wherein each total dose condition defines a condition for a total radiation dose for the respective irradiation region;
determining, by the processor, the number of single beam dose conditions, wherein one of the number of single beam dose conditions is assigned to a respective one of the number of beams and an irradiation region of the number of irradiation regions, the one single beam dose condition comprising a maximum allowed dose level for the respective one of the beams, and wherein the single beam dose condition assigned to the respective beam defines a condition for a beam dose as a function of the respective beam for the irradiation region; and
determining, by the processor, irradiation parameters for the number of beams as a function of the number of total dose conditions and of the number of single beam dose conditions.

2. The method as claimed in claim 1, wherein determining the irradiation parameters for the number of beams comprises minimizing a target function F(p), where $$F(p) = F_{tot}(p) + \sum_i F_i(p),$$

and wherein $P_{tot}(p)$ comprises an evaluation function that represents a fulfillment of the total dose conditions with the irradiation parameters, and $F_i(p)$ comprises an evaluation function that represents a fulfillment of the single beam dose conditions for a respective beam i of the number of beams with the irradiation parameters.

3. The method as claimed in claim 1, wherein determining the number of total dose conditions comprises capturing a user input of the at least one total dose condition for the respective one of the number of irradiation regions.

4. The method as claimed in claim 3, wherein the total dose condition comprises a maximum dose, a minimum dose, a dose-volume histogram, an average dose, an equivalent uniform dose (EUD), a biological target value, or a dose homogeneity.

5. The method as claimed in claim 1, wherein determining the number of single beam dose conditions comprises capturing a user input of the one single beam dose condition for the respective one of the number of beams and the irradiation region.

6. The method as claimed in claim 5, wherein the single beam dose condition comprises a maximum dose, a minimum dose, an average dose, or a dose homogeneity.

7. The method as claimed in claim 1, wherein determining the number of single beam dose conditions comprises automatically determining the number of single beam dose conditions as a function of a predetermined beam homogeneity factor, wherein the beam homogeneity factor defines for one of the number of irradiation regions a maximum difference between radiation doses introduced by the number of beams into the respective one of the number of irradiation regions.

8. The method as claimed in claim 7, further comprising capturing a user input that specifies the beam homogeneity factor.

9. The method as claimed in claim 8, further comprising capturing a user input of a beam homogeneity weighting, wherein determining the irradiation parameters comprises determining the irradiation parameters for each of the number of beams as a function of the number of total dose conditions, the number of single beam dose conditions, and the beam homogeneity weighting, and wherein the beam homogeneity weighting defines an importance of the single dose conditions in the determination of the irradiation parameters.

10. The method as claimed in claim 7, wherein the beam homogeneity factor comprises a fixed value.

11. The method as claimed in claim 7, further comprising capturing a user input of a beam homogeneity weighting, wherein determining the irradiation parameters comprises determining the irradiation parameters for each of the number of beams as a function of the number of total dose conditions, the number of single beam dose conditions, and the beam homogeneity weighting, and wherein the beam homogeneity weighting defines an importance of the single dose conditions in the determination of the irradiation parameters.

12. The method as claimed in claim 11, wherein determining the irradiation parameters for the number of beams comprises minimizing a target function F(p), where $$F(p) = F_{tot}(p) + HW \cdot \sum_i F_i(p, HF),$$

and wherein $P_{tot}(p)$ comprises an evaluation function that represents a fulfillment of the total dose conditions for the irradiation parameters, and $F_i(p,HF)$ comprises an evaluation function that is determined by the beam homogeneity factor and represents a fulfillment of the single beam dose conditions for a beam i of the number of beams for the irradiation parameters.

13. The method as claimed in claim 12, wherein the evaluation function $F_i(p,HF)$ determined by the beam homogeneity factor HF for the beam i is determined based on a predetermined minimum total dose level and a predetermined maximum total dose level, and further comprising determining a dose evaluation function for the beam using a maximum dose level $D_{max,i}$, where $D_{max,i}=D_{max,\,tot}*(1-HF/B)$, and a minimum dose level $D_{min,i}$, where $D_{min,i}=D_{min,tot}*HF/B$, wherein B is the number of beams.

14. The method as claimed in claim 1, further comprising detecting a user input of a single beam weighting, wherein determining the irradiation parameters comprises determining the irradiation parameters for each of the number of beams as a function of the number of total dose conditions, the number of single beam dose conditions, and the single beam weighting, and wherein the single beam weighting defines a relationship between the single beam dose conditions and the total dose conditions in the determination of the irradiation parameters.

15. The method as claimed in claim 14, wherein determining the irradiation parameters for the number of beams comprises minimizing a target function F(p), where $$F(p) = (1 - W) \cdot F_{tot}(p) + W \cdot \sum_i F_i(p),$$

and wherein $F_{tot}(p)$ comprises an evaluation function that represents a fulfillment of the total dose conditions for the irradiation parameters, and $F_i(p)$ comprises an evaluation function that represents a fulfillment of the single beam dose conditions for the beam in the irradiation parameters.

16. The method as claimed in claim 1, further comprising determining a number of beam-specific irradiation regions in the object to be irradiated, wherein the irradiation parameters for the number of beams are, for irradiation areas in which the beam-specific irradiation regions overlap, determined as a function of the total dose conditions, and for irradiation areas in which the beam-specific irradiation areas do not overlap, determined as a function of the single beam dose conditions.

17. The method as claimed in claim 1, wherein the total dose condition comprises a maximum dose, a minimum dose, a dose-volume histogram, an average dose, an equivalent uniform dose (EUD), a biological target value, or a dose homogeneity.

18. The method as claimed in claim 1, wherein the single beam dose condition comprises a maximum dose, a minimum dose, an average dose, or a dose homogeneity.

19. A method for determining a radiotherapy treatment plan for an irradiation of an object to be irradiated, wherein a number of irradiation regions are determined in the object to be irradiated, and wherein the object to be irradiated is irradiated with a number of beams from different directions, the method comprising:

provide a processor configured for determination of dose conditions and determination of irradiation parameters for the number of beams as a function of a number of total dose conditions and a number of single beam dose conditions;

determining, by the processor, the number of total dose conditions, wherein at least one of the number of total dose conditions is assigned to a respective one of the number of irradiation regions, and wherein each total dose condition defines a condition for a total radiation dose for the respective irradiation region;

determining, by the processor, the number of single beam dose conditions, wherein one of the number of single beam dose conditions is assigned to a respective one of the number of beams and an irradiation region of the number of irradiation regions, and wherein the single beam dose condition assigned to the respective beam defines a condition for a beam dose as a function of the respective beam for the irradiation region; and determining, by the processor, irradiation parameters for the number of beams as a function of the number of total dose conditions and of the number of single beam dose conditions, wherein determining the number of single beam dose conditions comprises automatically determining the number of single beam dose conditions as a function of a predetermined beam homogeneity factor, wherein the beam homogeneity factor defines for one of the number of irradiation regions a maximum difference between radiation doses introduced by the number of beams into the respective one of the number of irradiation regions.

* * * * *